Oct. 25, 1949. H. C. SWIM Plant Pat. 886
ROSE PLANT
Filed June 2, 1948
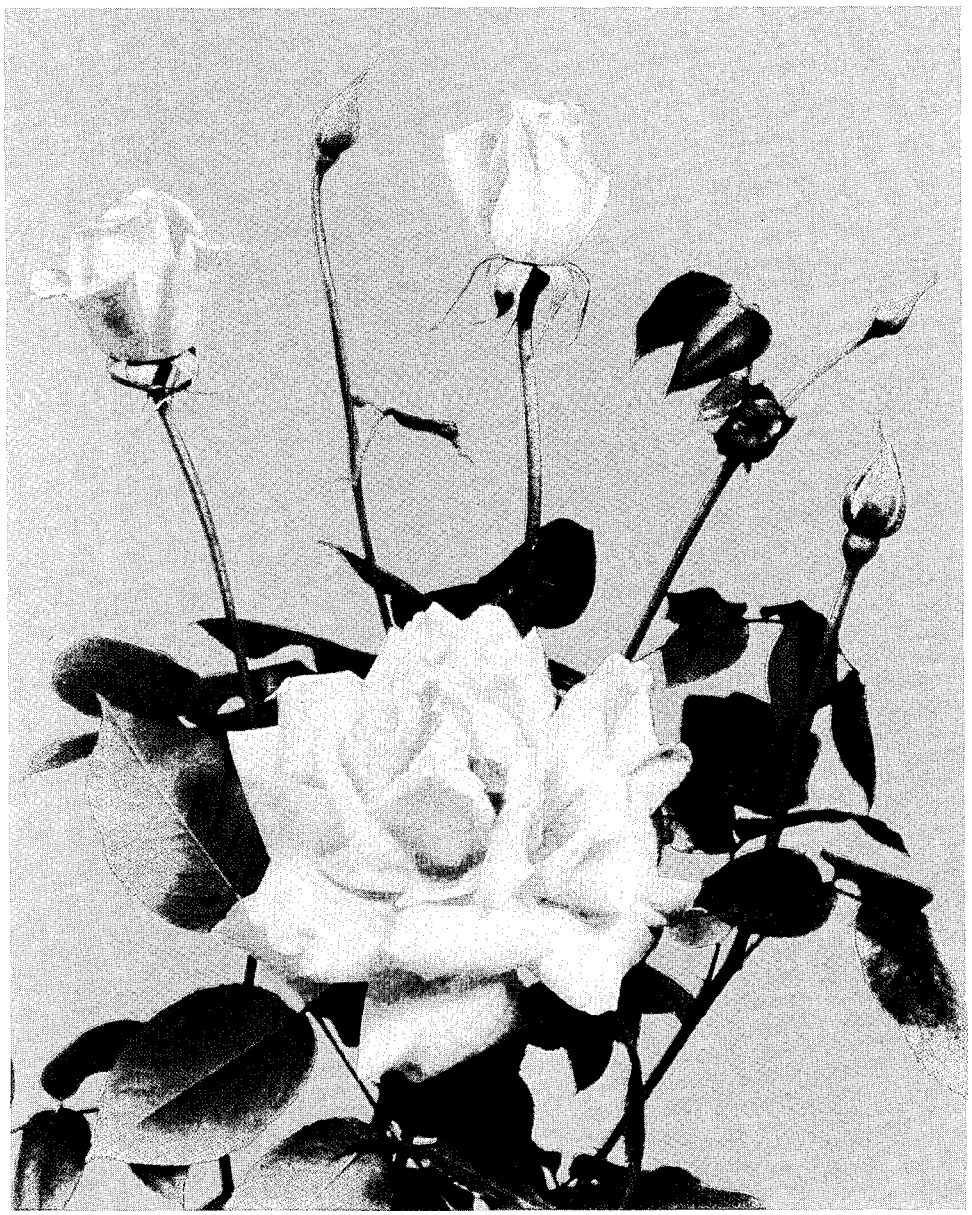
Inventor
H. C. Swim
By Robb & Robb
Attorneys Patented Oct. 25, 1949

Plant Pat. 886

UNITED STATES PATENT OFFICE

886

ROSE PLANT

Herbert C. Swim, Ontario, Calif., assignor, by mesne assignments, to Inter-State Nurseries, Inc., Hamburg, Iowa, a corporation of Delaware Application June 2, 1948, Serial No. 30,561

1 Claim. (Cl. 47—61)

The present invention relates to a new and distinct variety of rose plant, having the following combination of distinctive characteristics:

(1) An upright growing plant moderately branched with a normal amount of large, leathery, glossy leaves with more than average resistance to mildew.

(2) Buds of average to large size opening to large flowers five to six inches in diameter carrying unusual colors substantially as described and illustrated herein.

I know of no variety of rose in commerce that has this combination of characteristics. This combination resulted from crossing the well-known varieties "Mrs. Pierre S. du Pont" (seed parent) and "Charlotte Armstrong" (pollen parent).

This new variety differs from its seed parent, as follows:

(1) "Mrs. Pierre S. du Pont" is a yellow rose, whereas this new variety could, in popular terms, be described as Salmon-Orange.

(2) "Mrs. Pierre S. du Pont" is bushy and low growing, whereas this new variety is upright and only moderately bushy, growing much taller than its seed parent.

(3) The bud of this new variety is very much larger and more tapered than that of its seed parent.

(4) This new variety is more resistant to mildew than its seed parent.

This new variety differs also from its pollen parent:

(1) The color of the flower of this new variety could appropriately be described with the popular terms Salmon-Orange, whereas its pollen parent might appropriately be described with the popular term Red or Flame.

(2) This new variety has glossy foliage, whereas the foliage of "Charlotte Armstrong" is dull-surfaced.

(3) This new variety has no small prickles and only a moderate amount of large prickles, whereas its pollen parent has a large number of both small and large prickles.

Asexual reproduction shows that these characteristics hold true through succeeding propagations.

In the illustration are shown specimens of this new variety at different stages of development from bud to full blown flowers.

The following is a detailed description of the new variety, all references to color being in accordance with the Robert F. Wilson's Horticultural Colour Chart, except where indicated to be in accordance with Ridgway's Color Standards and Nomenclature:

Type: Bush; greenhouse; seedling; for cut flowers and garden decoration.

Class: Hybrid tea.

Breeding: Seedling.

*Seed parent.*—"Mrs. Pierre du Pont" (unpatented).

*Pollen parent.*—"Charlotte Armstrong" (Pl. Pat. No. 455).

Propagation: Holds its distinguishing characteristics through succeeding propagations by budding (other methods not being tried).

*Flower*

Locality where grown: Ontario, California (greenhouse).

Flowers borne: Usually singly, sometimes two or more, to stem; in irregular cluster; on normal strength long stems.

Quantity of bloom: Free in greenhouse.

Continuity: Continuous during growing season.

Fragrance: Slight tea to spicy.

Bud:

*Peduncle.*—Long; heavy; usually erect; moderately smooth: very few soft prickles. *Color*—Scheeles Green, Plate 860/2, page 175.

*Before calyx breaks.*—*Size*—medium to large. *Form*—medium length; pointed; with foliaceous appendages, few, gland-tipped cilia and bloom on the surface of the bud; with slender slightly cut foliaceous parts extending beyond the tip of the bud equal to one-fourth or more of its length.

*As calyx breaks.*—*Color*—between Begonia, Plate 619/1, page 146, and Empire Rose, Plate o621/1, page 183. *Sepals*—inner surface with fine, woolly tomentum; margins lined with stipitate glands unless adjacent sepals cover margin then only woolly tomentum is found on margin covered.

*As first petal opens.*—*Size*—average to large. *Form*—medium length to long; pointed to ovoid. *Color*—outside: base Aureolin, Plate 3, page 3, progressing toward the apex gradually becoming Vermillion, Plate 18/2, page 18, with a faint mottling of Mandarin Red, Plate 17/2, page 17, and Scarlet, Plate 19/2, page 19; inside: base Indian Yellow, Plate 6/1, page 6, progressing toward the apex it gradually changes to Carmine, Plate 21, page 21, with apex of petal Crimson, Plate 22/1, page 22. *Opening*—Opens up well. Is not retarded or prevented from opening by hot or dry weather.

Bloom:

*Size.*—When fully open, large; 5 inches to 6 inches.

*Petalage.*—Double; from 28 to 30 petals, plus one or two petaloids; arranged irregularly.

*Form.*—Full at first; becoming open to cupped; petals remaining at first somewhat loosely cupped, usually with upper one-half of lateral margins rolled abruptly outward—usually with apical point erect; becoming later, at maturity, more loosely flat cupped with lateral margins more tightly rolled outward.

Petals:

*Texture.*—Moderately leathery; with inside satiny and outside slightly shiny.

*Shape.*—Outside—broadly cuneate with apex pointed. Intermediate—cuneate with apex pointed. Inside—narrowly cuneate; scalloped irregular with apex rounded with one to two notches.

*Color.*—Colors may be modified by being washed with other colors.

This description of a newly opened flower was made from a rose grown in a greenhouse in the month of April, at Ontario, California:

*Color.*—*Outside petal*—outside surface: base near Indian Yellow, Plate 6/2, page 6, progressing to near Salmon, Plate 412/2, page 123, to Rose Pink, Plate 427/2, page 126, at upper margin of petal; inside surface: base Lemon Yellow, Plate 4/2, page 4, progressing to between Phlox Pink, Plate 625/2, page 77, and Neyron Rose, Plate 623/2, page 76, at upper half of petal. *Intermediate petal*—outside surface: base near Indian Yellow, Plate 6/2, page 6, progressing to Salmon, Plate 412/1, page 123, to Venetian Pink, Plate 420, page 125, at upper margin of petal; inside surface: base near Buttercup Yellow, Plate 5/2, page 5, progressing to between French Rose, Plate 520/1, page 136, and Neyron Rose, Plate 623/2, page 76, at upper half of petal. *Inner petal*—outside surface: base near Indian Yellow, Plate 6/2, page 6, progressing to Salmon, Plate 412/1, page 123, to Venetian Pink, Plate 420, page 125, at upper margin of petal; inside surface: base near Buttercup Yellow, Plate 5/2, page 5, progressing to between French Rose, Plate 520, page 136, and Carmine Rose, Plate 621/1, page 75, at upper half of margin.

This description was made from a rose that was open for three days in a greenhouse in the month of April, at Ontario, California:

*Color.*—*Outside petal*—outside surface: base Indian Yellow, Plate 6/3, page 6, progressing to Venetian Pink, Plate 420/1, page 125, at upper half of petal; inside surface: base Canary Yellow, Plate 2, page 2, progressing to near Neyron Rose, Plate 623/2, page 76, at upper half of petal. *Inside petal*—outside surface: base near Lemon Yellow, Plate 4/1, page 4, progressing to Rose Pink, Plate 427/2, page 126, at upper half of petal; inside surface: base Canary Yellow, Plate 2/1, page 2, progressing to Neyron Rose, Plate 623/1, page 76, at upper half of petal.

*General color effect.*—Newly opened flower— near Carmine Rose, Plate 621/1, page 75. Three days open—between Neyron Rose, Plate 623/3, page 76, and Phlox Pink, Plate 625/3, page 77.

*Behavior.*—Drop off cleanly; fading from Carmine Rose, Plate 621/1, page 75, to between Neyron Rose, Plate 623/3, page 76, and Phlox Pink, Plate 625/3, page 77.

*Flower longevity.*—On bush in greenhouse, three to four days in April. Cut roses grown in greenhouse kept at living-room temperatures three days in April.

*Reproductive organs*

Stamens: Many; arranged irregularly about pistils.

Filaments: Medium length to long; 1 to 2¼ cm. in length. *Color*—base near Saturn Red, Plate 13/2, page 13, becoming near and at anthers Cadmium Orange, Plate 8/3, page 8. All with anthers.

Anthers: Medium size to large; all open at once approximately. *Color*—Upper side—near Indian Yellow, Plate 6/3, page 6, bordered with Spanish Orange, Plate o10/2, page 103. Under side—near Buttercup Yellow, Plate 5/3, page 5, bordered with Spanish Orange, Plate o10/2, page 103. Under side—near Buttercup Yellow, Plate 5/3, page 5, bordered with Spanish Orange, Plate o10/2, page 103.

Pollen: Somewhat sparse to moderate. *Color*—near Indian Yellow, Plate 6/3, page 6.

Pistils: Average to many; approximately 40 in number.

Styles: Uneven, short to average length; average caliper; loosely bunched. *Color*—near Carmine, Plate 21, page 21.

Stigma: *Color*—Grayish white, somewhat translucent.

Ovaries: Usually all enclosed in calyx.

Sepals: From newly opened flower—medium length; spear shaped; reflexed and clasping about peduncle. *Color*—inside: Pod Green, Plate o61/2, page 120; outside: Pod Green, Plate o61/1, page 120.

*Plant*

Foliage:

*Leaves.*—Compound of usually 3 to 5 leaflets; normal in quantity; large size; moderately heavy to somewhat leathery and glossy.

*Leaflets.*—Shape—ovate to ovate-lanceolate with apex acute. Base—obtuse. Margin—doubly serrate.

*Color.*—*Mature*—upper surface: between Spinach Green, Plate o960, page 187, and Leek Green, Plate ooo858, page 197; under surface: between Spinach Green, Plate o960/3, page 187, and Leek Green, Plate ooo858/3, page 197. *Young*—upper surface: between Lettuce Green, Plate 861/3, page 176, and Spinach Green, Plate o960, page 187; under surface: near Lettuce Green, Plate 861/3, page 176, slightly overlaid with Rhodonite Red, Plate oo22/1, page 188.

*Rachis.*—Heavy. Upper side—grooved with some stipitate glands on edges. Under side—moderately prickly with few stipitate glands.

*Stipules.*—Medium length to long; medium-width, with moderately long points, turning out at an angle of less than 45°.

*Disease.*—More than average resistance to mildew.

Growth:

*Habit.*—Upright; moderately branched in greenhouse.

*Growth.*—Free.

*Canes.*—Medium caliper.

*Main stems.*— *Color*—near Spinach Green, Plate o960/3, page 187. *Large prickles*—several; medium length; hooked slightly downward; with medium length, moderately broad base. Color—between Clay Color, Plate XXIX (Ridgway), and Snuff Brown, Plate XXIX (Ridgway). *Small prickles and hairs*—none.

*Branches.*—*Color*—between Scheeles Green, Plate 860, page 175, and Spinach Green, Plate o960/3, page 187. *Large prickles*—several; medium length; hooked slightly downward; with medium length, moderately broad base. *Color*—near Scheeles Green, Plate 860/3, page 175. *Small prickles* — few. *Color* — near Scheeles Green, Plate 860/3, page 175. *Hairs*—none.

*New shoots.*—*Color*—Scheeles Green, Plate 860/2, page 175. *Large prickles* — few; medium length; hooked slightly downward; with medium length narrow to broad base. Color—between Pea Green, Plate 61/3, page 61, and Pod Green, Plate o61/3, page 120. *Small prickles and Hairs*—none.

I claim:

A new and distinct variety of rose plant, characterized as to novelty by its upright, moderately branched growing habit with a normal amount of large, leathery, glossy leaves and more than average resistance to mildew; and by its production of buds of average to large size, opening to large flowers five to six inches in diameter and of unusual colors, substantially as herein shown and described.

HERBERT C. SWIM.

No references cited